United States Patent
Shimizu et al.

(10) Patent No.: US 9,939,404 B2
(45) Date of Patent: Apr. 10, 2018

(54) CO SENSOR HAVING ELECTROMOTIVE FORCE RESPONSE

(71) Applicants: Nagasaki University, Nagasaki-shi (JP); Figaro Engineering Inc., Mino-shi (JP)

(72) Inventors: Yasuhiro Shimizu, Nagasaki (JP); Takeo Hyodo, Nagasaki (JP); Taro Ueda, Nagasaki (JP); Hirotaka Takeda, Nagasaki (JP); Kai Kamada, Nagasaki (JP)

(73) Assignees: Figaro Engineering Inc., Mino-shi (JP); Nagasaki University, Nagasaki-shi (JP)

( * ) Notice: Subject to any disclaimer, the term of this patent is extended or adjusted under 35 U.S.C. 154(b) by 204 days.

(21) Appl. No.: 15/016,487

(22) Filed: Feb. 5, 2016

(65) Prior Publication Data

US 2017/0227489 A1 Aug. 10, 2017

(51) Int. Cl.
*G01N 27/407* (2006.01)
*G01N 33/00* (2006.01)

(52) U.S. Cl.
CPC ..... *G01N 27/4071* (2013.01); *G01N 27/4075* (2013.01); *G01N 27/4076* (2013.01); *G01N 33/004* (2013.01)

(58) Field of Classification Search
CPC ............... G01N 27/406; G01N 27/407; G01N 27/4071; G01N 27/4075; G01N 33/004
See application file for complete search history.

(56) References Cited

FOREIGN PATENT DOCUMENTS

| JP | 10-239272 A | * | 9/1998 | ........... G01N 27/416 |
| JP | 2003-149195 A | * | 5/2003 | ........... G01N 27/409 |
| WO | 2015/002060 A1 | | 6/2014 | |

OTHER PUBLICATIONS

JPO computer-generated English language translation of Matsushita JP 2003-149195 A. Downloaded Oct. 19, 2017.*
JPO computer-generated English language translation of Yamazoe et al. JP 10-239272 A.*

* cited by examiner

*Primary Examiner* — Alexander S Noguerola
(74) *Attorney, Agent, or Firm* — The Webb Law Firm

(57) ABSTRACT

A CO sensor includes a solid electrolyte substrate, a sensing electrode, and a reference electrode, and outputs electromotive forces in accordance with CO concentrations. The sensing electrode and the reference electrode are provided on the same surface of the solid electrolyte substrate. The sensing electrode contains a metal oxide such as $Bi_2O_3$ that generates a positive electromotive force response when coming into contact with CO. The reference electrode contains a metal oxide such as $CeO_2$ that generates a negative electromotive force response when coming into contact with CO.

5 Claims, 9 Drawing Sheets

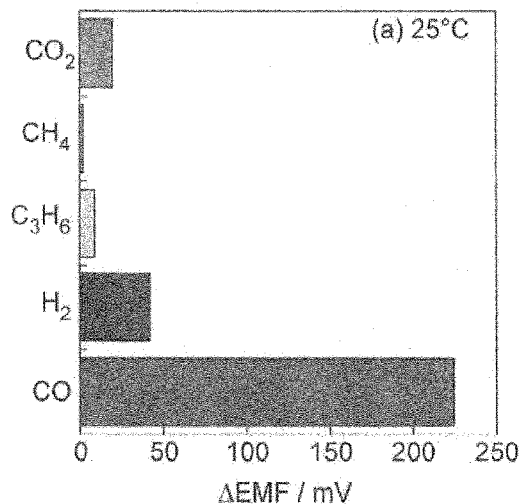
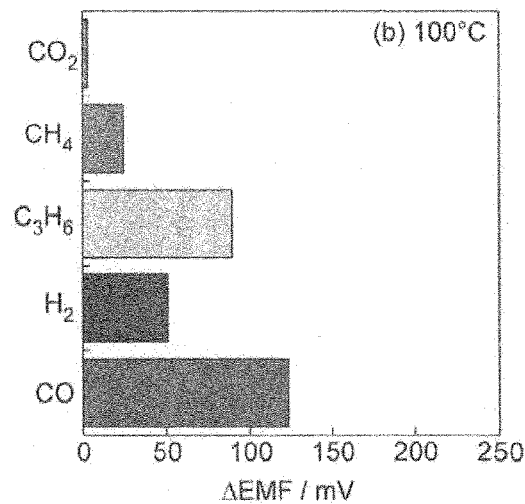
FIG. 9(a)          FIG. 9(b)
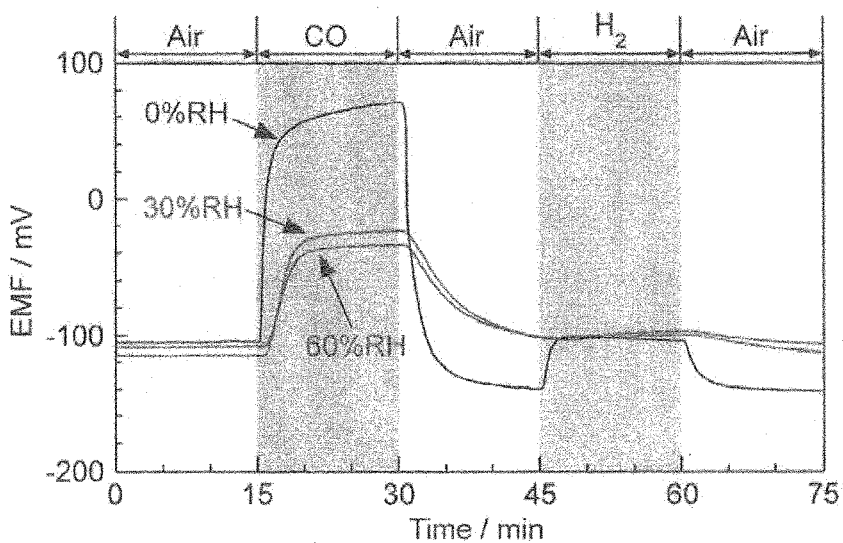
FIG. 10

CO SENSOR HAVING ELECTROMOTIVE FORCE RESPONSE

BACKGROUND OF THE INVENTION

Field of the Invention

This invention relates to a CO sensor having an electromotive force response that operates at room temperature.

Description of the Related Arts

Shimizu, Hyodo, and Takeda proposed a CO sensor in which a Pt—$Bi_2O_3$ sensing electrode and a Pt reference electrode are provided on the same surface of a solid electrolyte substrate made of NASICON (WO2015/2060A). This CO sensor outputs electromotive forces between the sensing electrode and the reference electrode, and has a significant response to CO at room temperature. Furthermore, in this CO sensor, the sensing electrode and the reference electrode can be provided on the same surface of the solid electrolyte substrate, and it is not necessary to shield the reference electrode from an atmosphere to be analyzed. Moreover, this CO sensor can operate in a dry atmosphere, and a water reservoir for supplying water vapor to the sensing electrode is not required. Accordingly, this CO sensor has a simple structure.

SUMMARY OF THE INVENTION

It is an object of the present invention to further increase a response to CO by improving reference electrode materials.

A CO sensor according to an aspect of the present invention includes a solid electrolyte substrate, a first electrode, and a second electrode, and outputs electromotive forces in accordance with CO concentrations, wherein the first electrode and the second electrode are provided on a same surface of the solid electrolyte substrate, the first electrode contains a first metal oxide that generates a positive electromotive force response when coming into contact with CO, and the second electrode contains a second metal oxide that generates a negative electromotive force response when coming into contact with CO.

It is preferable that the second metal oxide is at least one selected from the group consisting of $CeO_2$, $V_2O_5$, $WO_3$, and $Ta_2O_5$.

It is more preferable that the first metal oxide is at least one selected from the group consisting of $Bi_2O_3$, $Cr_2O_3$, and $La_2O_3$.

It is preferable that the first electrode contains Pt and the first metal oxide, and the second electrode contains Pt and the second metal oxide. Here, "containing Pt" includes "containing a Pt alloy".

It is particularly preferable that the first electrode is a mixture of Pt and the first metal oxide, and the second electrode is a mixture of Pt and the second metal oxide.

The CO sensor according to the aspect of the present invention operates at room temperature, but is not particularly limited thereto. The electric potential of the first electrode has a positive response to CO, the electric potential of the second electrode has a negative response to CO, and the CO sensor as a whole has a significant response to CO. It depends on the types of the metal oxides in the electrodes whether the response is positive or negative. For example, $CeO_2$, $V_2O_5$, $WO_3$, and $Ta_2O_5$ have a negative response, and $Bi_2O_3$, $Cr_2O_3$, and $La_2O_3$ have a positive response. Although these metal oxides may be used alone to form the electrode, it is preferable that both the first electrode and the second electrode contain Pt. It is particularly preferable that the first electrode is an electrode made of a mixture of Pt and the first metal oxide, and the second electrode is an electrode made of a mixture of Pt and the second metal oxide.

BRIEF DESCRIPTION OF THE DRAWINGS

FIGS. 9(a) and 9(b) show characteristic diagrams indicating responses of a CO sensor having a Pt(15$Bi_2O_3$) sensing electrode and a Pt reference electrode to various 300 ppm gasses. FIG. 9(a) shows responses at 25° C., and FIG. 9(b) shows responses at 100° C.

FIG. 10 is a response diagram of a CO sensor having a Pt(1$Bi_2O_3$) sensing electrode and a Pt reference electrode to CO and $H_2$ at 25° C. at relative humidities of 0%, 30%, and 60%.

DETAILED DESCRIPTION OF PREFERRED EMBODIMENTS

Hereinafter, various embodiments will be described. It should be noted that an embodiment having a reference electrode that is made of only Pt and contains no metal oxides is intended to explain roles of a first metal oxide and a second metal oxide.

Structure of the CO Sensor

Figure 1:
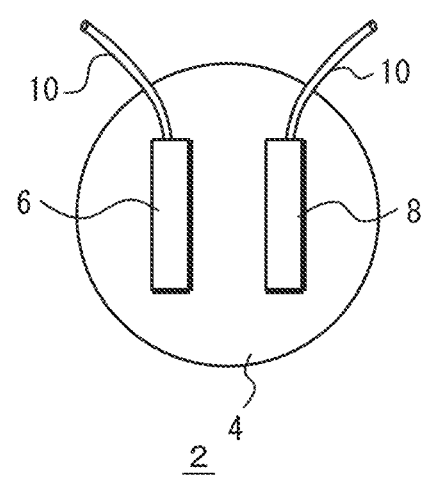
FIG. 1 is a plan view of a CO sensor.

FIG. 1 shows a structure of a CO sensor 2 of an embodiment. A sensing electrode 6 (the first electrode) and a reference electrode 8 (the second electrode) are provided on the same surface of a solid electrolyte substrate 4 made of NASICON ($Na_3Zr_2Si_2PO_{12}$), which is a $Na^+$ ion conductor. It should be noted that 10 denotes leads made of Pt or the like that are attached to the electrodes 6 and 8, and the electrodes 6 and 8 can be configured to have any shape such as a comb-teeth shape. The solid electrolyte substrate 4 may be made of any type of ion conductor, and examples thereof include another $Na^+$ conductor such as $\beta$-$Al_2O_3$, an anion conductor such as $LaF_3$, a $Li^+$ conductor such as LISICON, a proton conductor including a proton conductive polymer or a metal oxide, and a hydroxide ion conductor including a hydroxide ion conductive polymer or a metal oxide.

The sensing electrode 6 is a mixture of a first metal oxide and Pt or a Pt alloy such as Pt—Ru, Pt—Rh or Pt—Au, and in an embodiment, the sensing electrode 6 is a thick film of a mixture of Pt and the first metal oxide. However, the sensing electrode 6 may be a thin film of the above-mentioned mixture or an electrode having two or more layers in which a layer of the first metal oxide is provided onto a Pt or Pt alloy layer, the Pt or Pt alloy layer being provided on the solid electrolyte substrate 4. Similarly, the reference electrode 8 is a mixture of a second metal oxide and Pt or a Pt alloy such as Pt—Ru or Pt—Rh, and in an embodiment, the reference electrode 8 is a thick film of a mixture of Pt and the second metal oxide. However, the reference electrode 8 may be a thin film of the above-mentioned mixture. The reference electrode 8 may also be an electrode having two or more layers in which a layer of the second metal oxide is provided onto a Pt or Pt alloy layer, the Pt or Pt alloy layer being provided on the solid electrolyte substrate 4. In this specification, the Pt alloy is an alloy in which the mol concentration of Pt in metal components is preferably 50 mol % or more, and more preferably 70 mol % or more.

The sensing electrode 6 is the first electrode in which an electric potential has a positive response when the first electrode comes into contact with CO, the reference electrode 8 is the second electrode in which an electric potential has a negative response when the second electrode comes into contact with CO, and the sum of these responses in absolute values is the response as a whole. Moreover, the difference between the electric potential of the sensing electrode and the electric potential of the reference electrode is electromotive force, EMF, and the response is a change in the electromotive force, ΔEMF. The composition of the electrode made of the mixture is expressed as Pt($15Bi_2O_3$) or the like, where the type of metal oxide and the concentration thereof in the electrode in mass % are shown in parentheses. In this case, the concentration of Pt is 85 mass % and the concentration of $Bi_2O_3$ is 15 mass %. In an expression such as Pt($15Bi_2O_3$)/Pt($15CeO_2$), a first half, Pt($15Bi_2O_3$), indicates the composition of the sensing electrode, and a second half, Pt($15CeO_2$), indicates the composition of the reference electrode. The concentration of the first metal oxide in the sensing electrode 6 is set to 0.01 mass % or more and 30 mass % or less, for example, and preferably 0.1 mass % or more and 20 mass % or less. Similarly, the concentration of the second metal oxide in the reference electrode 8 is set to 0.01 mass % or more and 30 mass % or less, for example, and preferably 0.1 mass % or more and 20 mass % or less.

Production of the CO Sensors

The sensing electrode 6 and the reference electrode 8 having a film thickness of 20 μm, for example, were made by preparing a paste in which Pt and powder of the first metal oxide were mixed and another paste in which Pt and powder of the second metal oxide were mixed, applying them onto the solid electrolyte substrate 4 made of NASICON, attaching the Pt leads 10 thereto, and calcining them in air at 700° C. The calcining may be performed at any temperature and in any atmosphere, and the electrodes 6 and 8 may have any film thickness. Instead of the thick-film electrodes obtained by calcining the pastes, a mixture target of Pt and a metal oxide such as $Bi_2O_3$ may be used to form a thin-film sensing electrode, and similarly, a mixture target of Pt and a metal oxide such as $CeO_2$ may be used to form a thin-film reference electrode. Alternatively, after first layers of the sensing electrode 6 and the reference electrode 8 are formed using a Pt paste, a surface layer of the sensing electrode 6 may be formed by laminating a paste of $Bi_2O_3$ or the like on the first layer and calcining them, and a surface layer of the reference electrode 8 may be formed by laminating a paste of $CeO_2$ or the like on the first layer of the reference electrode 8 and calcining them.

Interface Between Electrode and Solid Electrolyte

Figure 2:
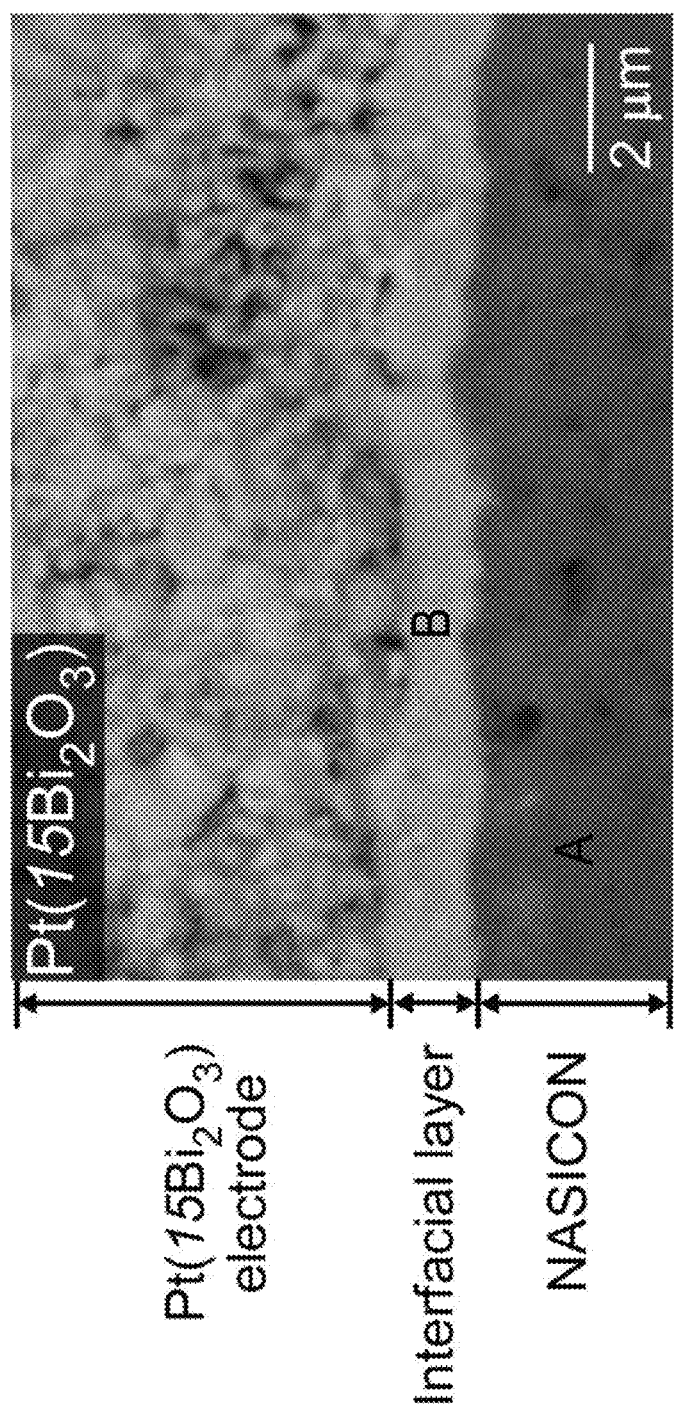
FIG. 2 is an electron micrograph of a Pt(15$Bi_2O_3$) electrode and a NASICON substrate.
Figure 3:
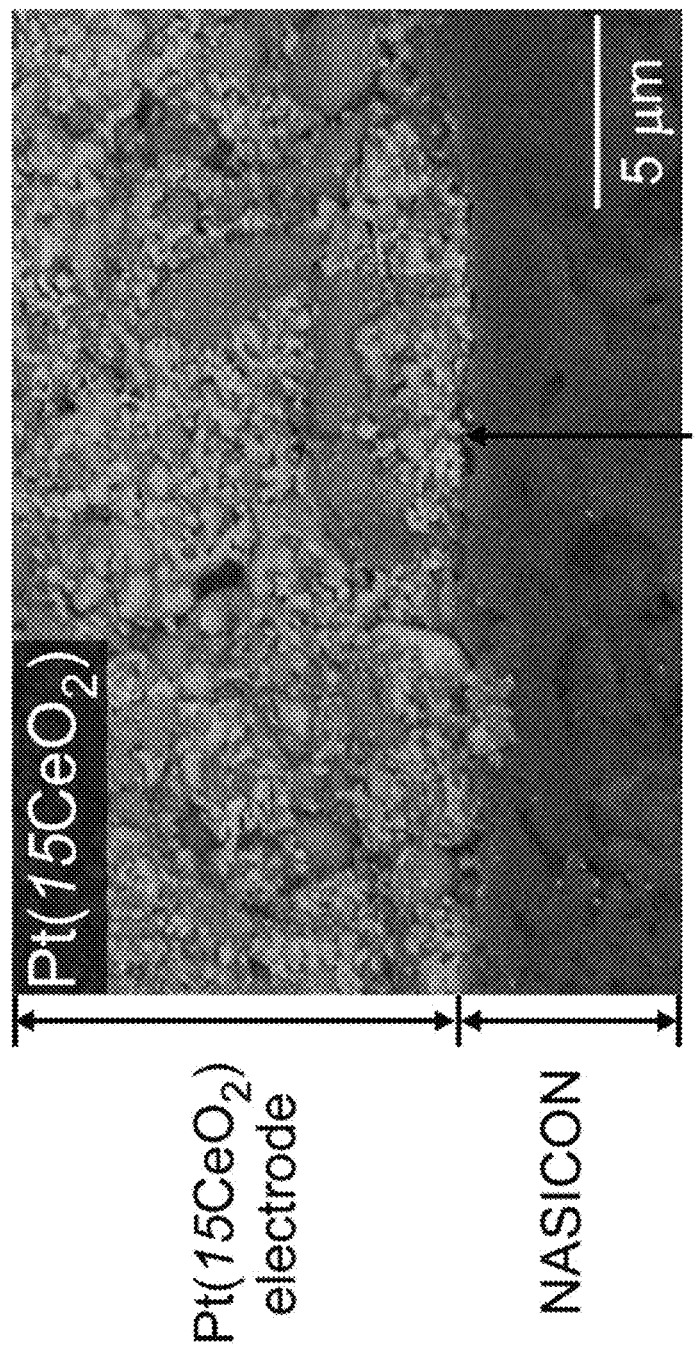
FIG. 3 is an electron micrograph of a Pt(15$CeO_2$) electrode and a NASICON substrate.
Figure 4:
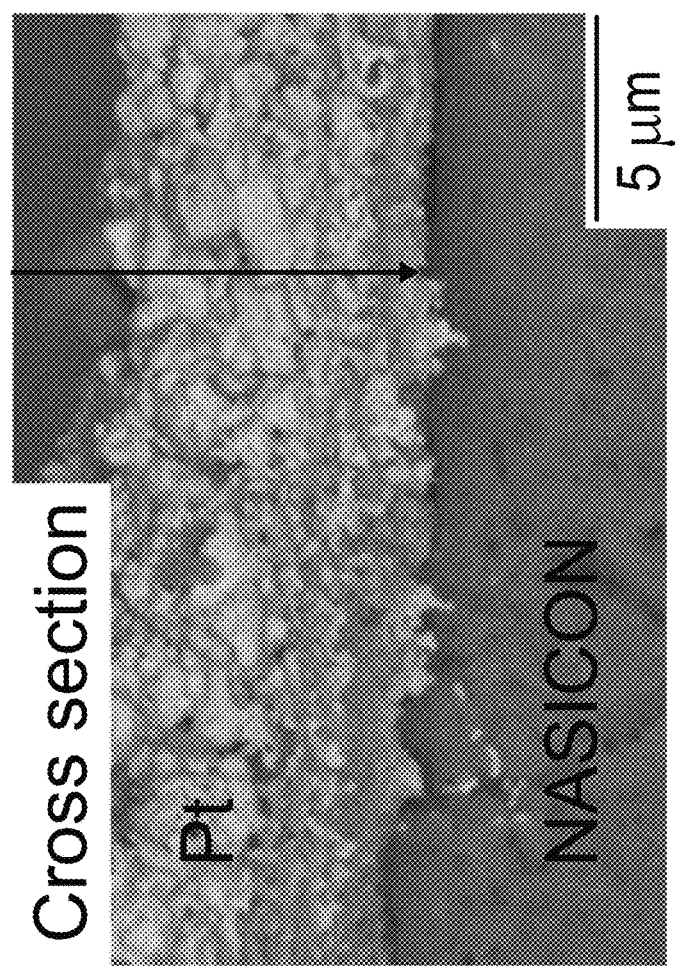
FIG. 4 is an electron micrograph of a Pt electrode and a NASICON substrate.

FIG. 2 shows an interface between a Pt($15Bi_2O_3$) sensing electrode and the solid electrolyte substrate 4, FIG. 3 shows an interface between a Pt($15CeO_2$) reference electrode and the solid electrolyte substrate 4, and FIG. 4 shows an interface between a Pt reference electrode and the solid electrolyte substrate 4. There was an interfacial layer B between the Pt($15Bi_2O_3$) sensing electrode and the solid electrolyte substrate 4. Table 1 shows the composition of NASICON shown as A in FIG. 2 and the composition of the interfacial layer B. In the interfacial layer B, the concentrations of Na and Si in NASICON decreased, and Bi and Pt were detected in place of them. When metal oxides other than $Bi_2O_3$ were used, such an interfacial layer was not detected.

TABLE 1

| Element | Composition (mol %) | |
| --- | --- | --- |
| | NASICON A | Intermediate Layer B |
| Na | 32 | 4.2 |
| Si | 35 | 5.5 |
| P | 15 | 23 |
| Zr | 18 | 16 |
| Bi | 0 | 28 |
| Pt | 0 | 23 |

A CO sensor was brought into contact with an atmosphere obtained by adding a gas such as CO or $H_2$ to a dry air from which $CO_2$ and water vapor were sufficiently removed, and electromotive force responses were measured. The CO concentrations were generally 300 ppm, and the measurement temperatures were generally 25° C.

Gas Response

Figure 5:
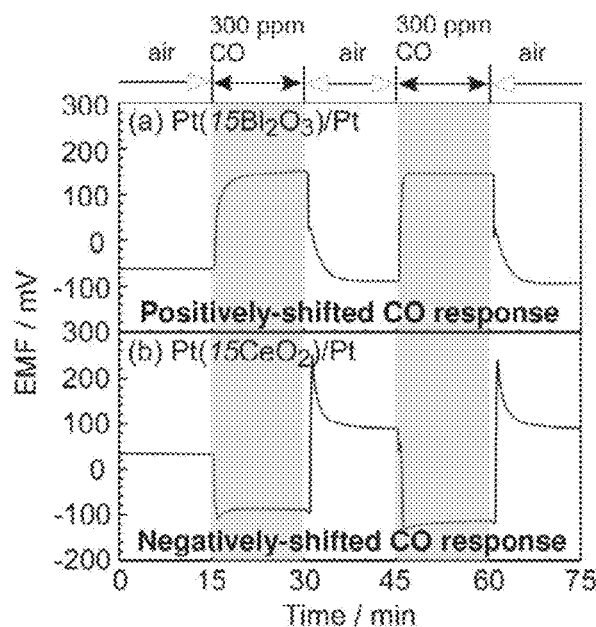
FIG. 5 shows response diagrams of CO sensors to CO at 25° C.
Figure 6:
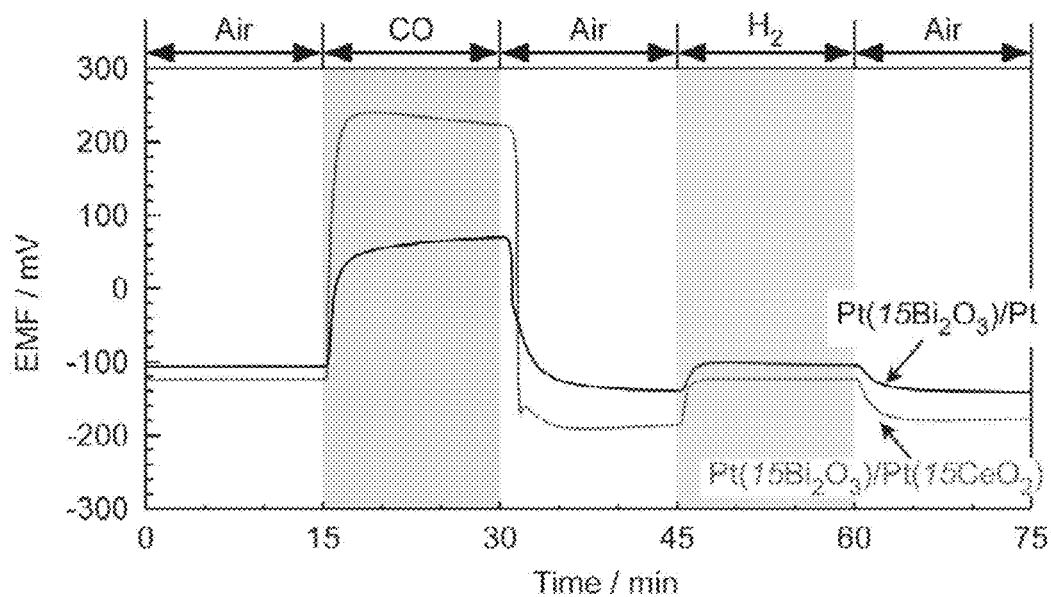
FIG. 6 is a response diagram of a CO sensor having a Pt(15$Bi_2O_3$) sensing electrode and a Pt(15$CeO_2$) reference electrode to CO and $H_2$ at 25° C.

FIG. 5A shows responses of a CO sensor having a Pt($15Bi_2O_3$) sensing electrode and a Pt reference electrode and a CO sensor having a Pt($15CeO_2$) sensing electrode and a Pt reference electrode to 300 ppm CO. The responses, ΔEMFs, of the Pt($15Bi_2O_3$) electrode and the Pt($15CeO_2$) electrode to CO have opposite signs. A CO sensor of an embodiment having a Pt($15Bi_2O_3$) sensing electrode and a Pt($15CeO_2$) reference electrode had a significant response corresponding to the sum of two changes in electromotive force (FIG. 6).

Figure 7:
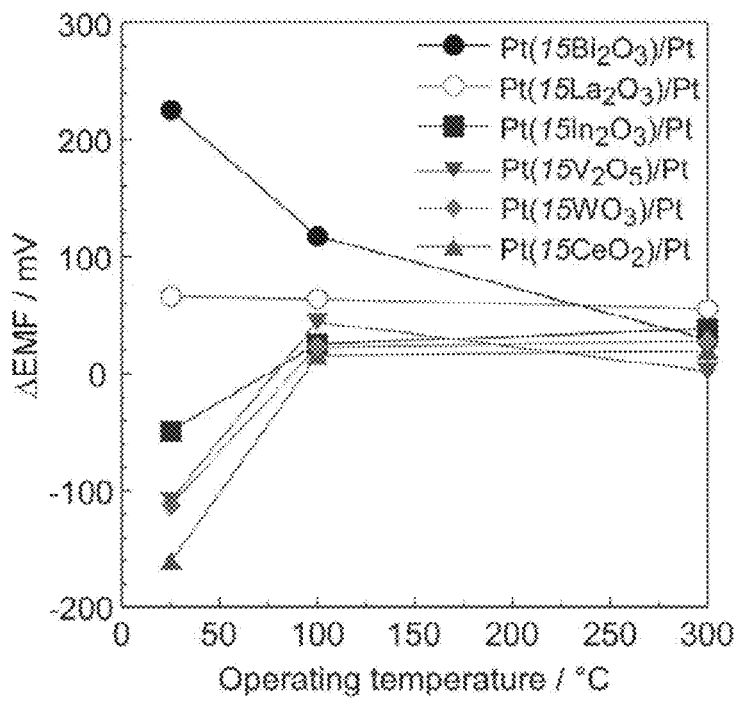
FIG. 7 is a characteristic diagram regarding various sensing electrode materials indicating responses to 300 ppm CO at 25° C. to 300° C.

FIG. 7 shows responses to 300 ppm CO depending on the types of metal oxides in the sensing electrodes. All of the metal oxides had a significant response at room temperature. The electromotive force of some metal oxides ($Bi_2O_3$ and $La_2O_3$) was positively changed by CO at room temperature, and the electromotive force in other metal oxides ($CeO_2$, $WO_3$, $V_2O_5$, and $In_2O_3$) was negatively changed. Table 2 shows the results from various metal oxides (contained in the sensing electrode in an amount of 15 mass %) at 30° C. $Bi_2O_3$, $Cr_2O_3$, and $La_2O_3$ are preferable as the first metal oxide, and $CeO_2$, $V_2O_5$, $WO_3$, and $Ta_2O_5$ are preferable as the second metal oxide.

TABLE 2

Responses to 300 ppm CO in Dry Air at 30° C. for Various Metal Oxides

| Metal Oxides | ΔEMF (mV) |
|---|---|
| $Bi_2O_3$ | 235 |
| $Cr_2O_3$ | 253 |
| $La_2O_3$ | 55 |
| CuO | 43 |
| $CeO_2$ | −202 |
| $V_2O_5$ | −149 |
| $WO_3$ | −125 |
| $Ta_2O_5$ | −109 |
| $Al_2O_3$ | −99 |
| NiO | −78 |
| $In_2O_3$ | −63 |
| $Mn_2O_3$ | −47 |

Model for the Detection Mechanism

Since NASICON, which is a $Na^+$ conductor, is used in the substrate, we assume that CO is oxidized according to the following reaction on the Pt surfaces of both the sensing electrode and the reference electrode.

$$CO + Na_2O \rightarrow 2Na^+ + 2e^- + CO_2 \quad (1)$$

We assume that the electric potentials of the sensing electrodes and the reference electrodes are reduced by this reaction, and the reaction 1) rapidly progresses in the Pt-containing electrodes due to the strong catalytic activity of Pt. Further, we assume that a reaction 2) similar to the reaction 1) progresses in a proton conductor, and a reaction 3) in which Na is substituted by Li progresses in a $Li^+$ ion conductor. However, with the reactions 1) to 3), it is difficult to explain the electric potential of the sensing electrode containing $Bi_2O_3$ or the like is positively shifted by CO.

$$CO + H_2O \rightarrow 2H^+ + 2e^- + CO_2 \quad (2)$$

$$CO + Li_2O \rightarrow 2Li^+ + 2e^- + CO_2 \quad (3)$$

It is very likely that when the sensing electrode contains $Bi_2O_3$, a reaction 4) occurs.

$$\delta CO + Bi_2O_3 + 2\delta Na^+ + 2\delta e^- \rightarrow Bi_2O_{3-2\delta} + \delta Na_2O + \delta CO_2 \quad (4)$$

The electric potential of the sensing electrode is positively shifted by this reaction 4), and assuming that the electric potential of the sensing electrode is determined by a hybrid potential by the reaction 4) and the reaction 1), the result from the $Pt(Bi_2O_3)$ sensing electrode is explained. It should be noted that a positive response of an $Au(1Bi_2O_3)$ sensing electrode to CO was smaller than that of a $Pt(1Bi_2O_3)$ sensing electrode. This suggests that the reaction 4) also easily progresses in a Pt-containing electrode.

Regarding $CeO_2$ in the reference electrode, it is far more likely that the reaction 1) is promoted by $CeO_2$, resulting in a further decrease in the electric potential of the reference electrode, rather than a new type of reaction occurs. A reaction of extracting oxygen from $CeO_2$, or the like is unlikely to occur. Therefore, assuming that the reaction of 4) is promoted by $Bi_2O_3$ or the like in the sensing electrode and the reaction of 1) is promoted by $CeO_2$ in the reference electrode, a significant response to CO can be explained.

Moreover, when containing Pt, both the sensing electrode and the reference electrode have a significant response, and therefore, we assume that a catalytic activity of Pt contributes to the responses.

Results Regarding $Bi_2O_3$ Sensing Electrode

Figure 8:
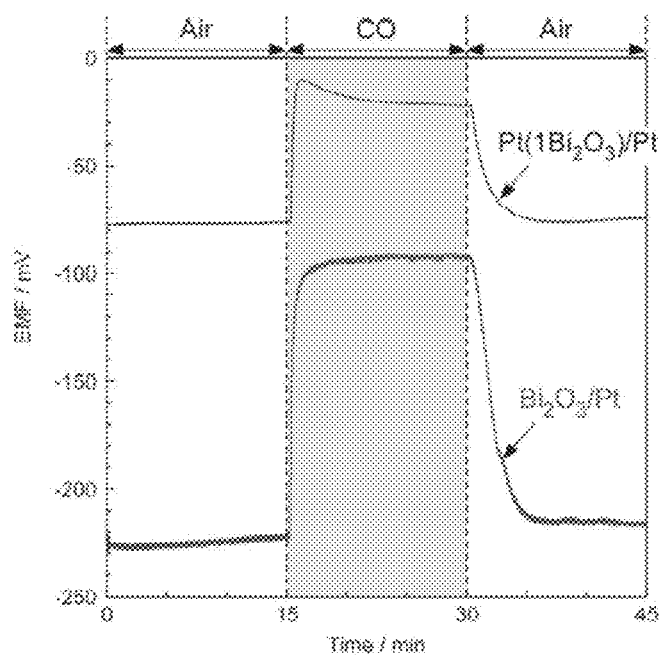
FIG. 8 is a response diagram of two CO sensors that differ in sensing electrode materials to CO at 25° C.

Since $Bi_2O_3$ has an electron conductivity, a sensing electrode can be made of $Bi_2O_3$ without Pt. FIG. 8 shows a response of a $Bi_2O_3$ electrode containing no Pt to 300 ppm CO in a dry atmosphere at 25° C. It can be inferred from this result that an electrode in which a Pt mesh supports a metal oxide, or the like can detect CO.

Response to Various Gases

FIGS. 9(a) and 9(b) show responses of a $Pt(1Bi_2O_3)/Pt$ to atmospheres including various 300 ppm gasses. The selective response to CO can be obtained at room temperature. The response to $CO_2$ is small, suggesting that the response to CO does not depend on the ratio of the concentrations of $CO_2$ generated by the reactions 1) to 4) in the sensing electrode and the reference electrode.

FIG. 10 shows responses of the $Pt(1Bi_2O_3)/Pt$ to 300 ppm CO and $H_2$. Although both the response to CO and the response to $H_2$ decreased in a moisturized atmosphere, the response to CO relative to the response to $H_2$ was higher in a moisturized atmosphere than in a dry atmosphere.

Influence of Metal Oxide Concentrations

Figure 11:
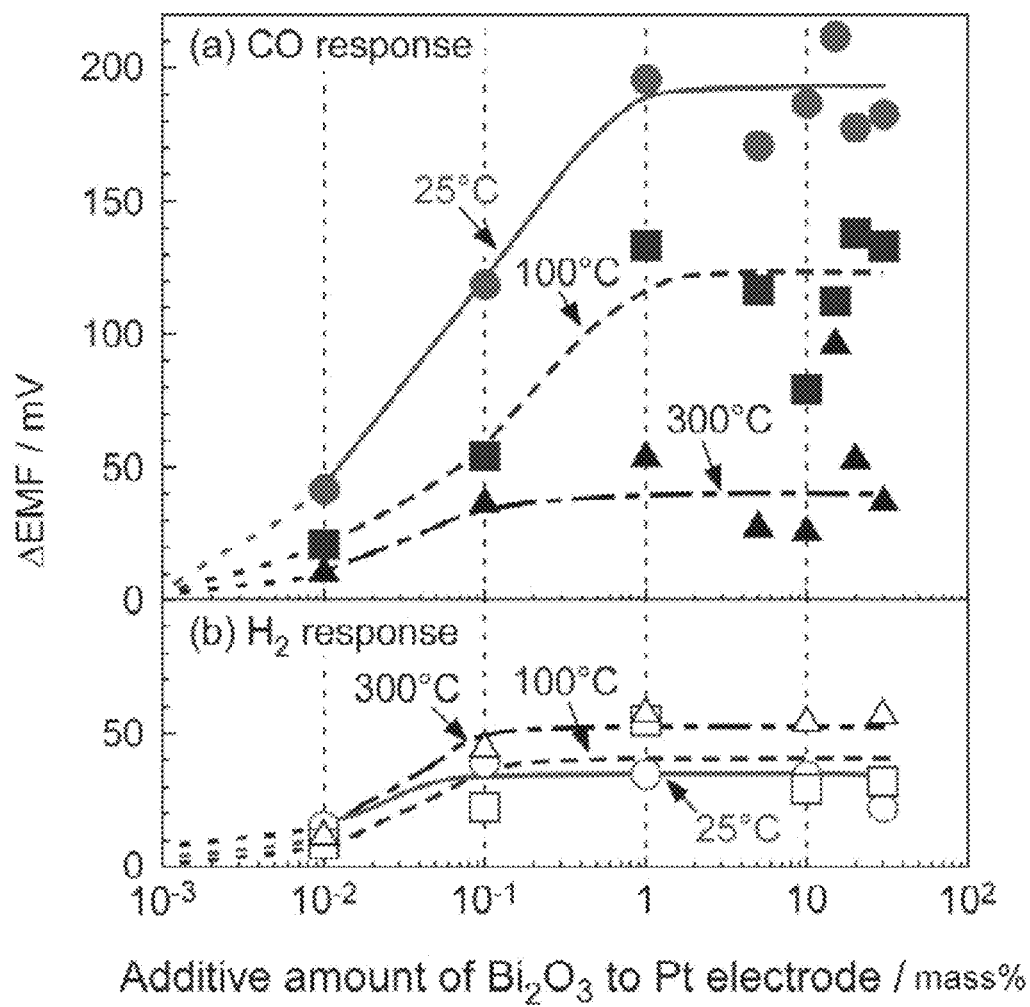
FIG. 11 shows characteristic diagrams indicating influences of the $Bi_2O_3$ concentration in a sensing electrode on responses of a CO sensor having a Pt($Bi_2O_3$) sensing electrode and a Pt reference electrode to CO and $H_2$.

FIG. 11 shows the $Bi_2O_3$ concentration dependence of responses of a $Pt(Bi_2O_3)/Pt$ to 300 ppm CO and $H_2$. Even when the concentration of $Bi_2O_3$ was 0.01 mass %, the response to CO was generated. When the concentration was 0.1 mass % or more, the response increased, and when the concentration was 1 mass % or more, the response was substantially constant. When other metal oxides such as $CeO_2$ were used, the responses to CO depended on the metal oxide concentration in substantially the same manner as the case where $Bi_2O_3$ was used.

Influence of Carbon Monoxide Concentrations

Figure 12:
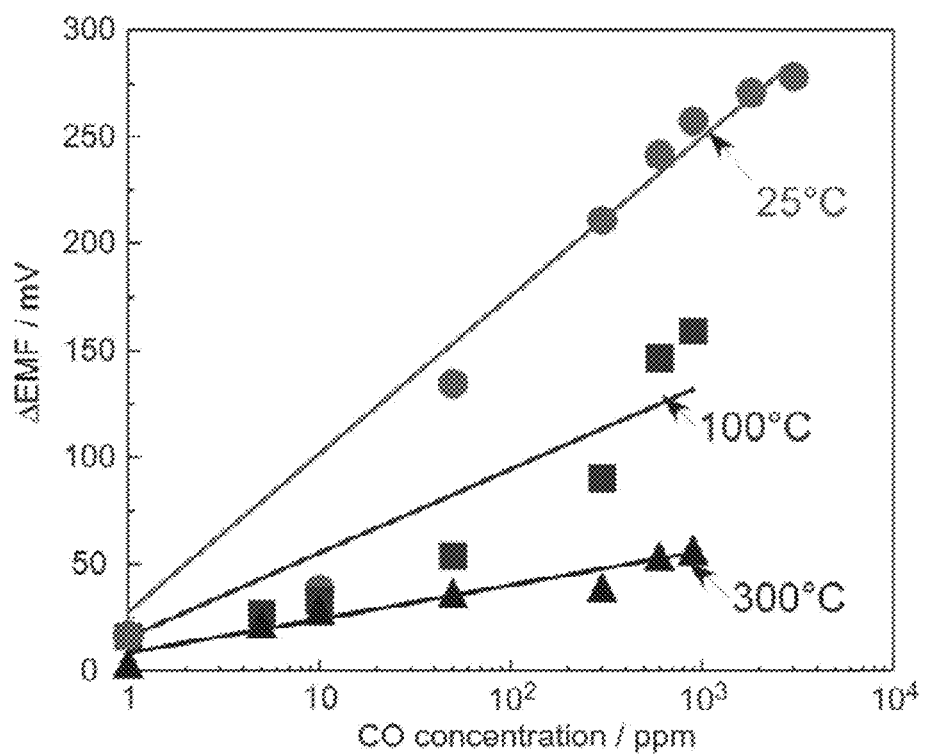
FIG. 12 is a characteristic diagram indicating CO concentration dependence of responses of a CO sensor having a Pt(1$Bi_2O_3$) sensing electrode and a Pt reference electrode to CO.

FIG. 12 shows the CO concentration dependence of responses of a CO sensor having a $Pt(Bi_2O_3)/Pt$. The responses linearly changed with respect to logarithms of the CO concentrations. A maximum response was obtained at 25° C., and CO at about 1 ppm could be detected. When other metal oxides such as $CeO_2$ were used, responses linearly changed with respect to logarithms of the CO concentrations similarly.

What is claimed is:

1. A CO sensor comprising:
   a solid electrolyte substrate;
   a first electrode; and
   a second electrode,
   the CO sensor outputting electromotive forces in accordance with CO concentrations,
   wherein the first electrode and the second electrode are provided on a same surface of the solid electrolyte substrate,
   the first electrode contains a first metal oxide that is a binary compound comprised of a first metal element and oxygen and generates a positive electromotive force response when coming into contact with CO, and
   the second electrode contains a second metal oxide that is a binary compound comprised of a second metal element and oxygen and generates a negative electromotive force response when coming into contact with CO.

2. The CO sensor according to claim 1, wherein the second metal oxide is at least one selected from the group consisting of $CeO_2$, $V_2O_5$, $WO_3$, and $Ta_2O_5$.

3. The CO sensor according to claim 2, wherein the first metal oxide is at least one selected from the group consisting of $Bi_2O_3$, $Cr_2O_3$, and $La_2O_3$.

4. The CO sensor according to claim 3,
   wherein the first electrode contains Pt and the first metal oxide, and
   the second electrode contains Pt and the second metal oxide.

5. The CO sensor according to claim 4,
wherein the first electrode is a mixture of Pt and the first metal oxide, and
the second electrode is a mixture of Pt and the second metal oxide.

* * * * *